(12) United States Patent
Voigtmann et al.

(10) Patent No.: US 9,572,486 B2
(45) Date of Patent: Feb. 21, 2017

(54) DEVICE AND METHOD FOR CHECKING HUMAN VISION

(71) Applicants: VOIGTMANN GMBH, Nuremberg (DE); TALKINGEYES & MORE GMBH, Erlangen (DE); FRIEDRICH-ALEXANDER-UNIVERSITAT ERLANGEN-NURNBERG, Erlangen (DE); UNIVERSITATSKLINIKUM ERLANGEN, Erlangen (DE)

(72) Inventors: Peter Voigtmann, Rückersdorf (DE); Bernhard Hoher, Erlangen (DE); Bernhard Schmauss, Theisseil (DE); Georg Michelson, Baiersdorf (DE)

(73) Assignees: VOIGTMANN GMBH, Nuremberg (DE); TALKINGEYES & MORE GMBH, Erlangen (DE); FRIEDRICH-ALEXANDER-UNIVERSITAT ERLANGEN-NURNBERG, Erlangen (DE); UNIVERSITATSKLINIKUM ERLANGEN, Erlangen (DE)

( * ) Notice: Subject to any disclaimer, the term of this patent is extended or adjusted under 35 U.S.C. 154(b) by 0 days.

(21) Appl. No.: 14/443,910

(22) PCT Filed: Nov. 20, 2013

(86) PCT No.: PCT/EP2013/074290
§ 371 (c)(1),
(2) Date: May 19, 2015

(87) PCT Pub. No.: WO2014/079885
PCT Pub. Date: May 30, 2014

(65) Prior Publication Data
US 2015/0320306 A1 Nov. 12, 2015

(30) Foreign Application Priority Data
Nov. 21, 2012 (DE) ........................ 10 2012 022 662

(51) Int. Cl.
| | | |
|---|---|---|
| A61B 3/08 | (2006.01) |
| A61B 3/02 | (2006.01) |
| A61B 3/00 | (2006.01) |
| A61B 3/032 | (2006.01) |
| A61B 3/09 | (2006.01) |

(52) U.S. Cl.
CPC ............... *A61B 3/08* (2013.01); *A61B 3/032* (2013.01); *A61B 3/09* (2013.01)

(58) Field of Classification Search
USPC .................................................. 351/200–246
See application file for complete search history.

(56) References Cited

U.S. PATENT DOCUMENTS 5,568,209 A * 10/1996 Priester .................. A61B 3/032
351/239
5,825,456 A 10/1998 Tabata et al.
(Continued)

FOREIGN PATENT DOCUMENTS

DE 4222395 A1 1/1994
DE 19501415 A1 8/1996
(Continued)

OTHER PUBLICATIONS

International Preliminary Report on Patentability (IPRP) dated May 21, 2015, for PCT/EP2013/074290.
(Continued)

*Primary Examiner* — Mohammed Hasan
(74) *Attorney, Agent, or Firm* — Bacon & Thomas, PLLC

(57) ABSTRACT

The invention relates to a device and a method for checking human vision, comprising an image-generating module for generating any test images, an imaging module, used to image the test image provided by the image-generating module on the retina of the eye as a stimulus, the imaging module containing at least one optical component having variable focal length, such that the test image of the image-generating module is perceptible to the eye from virtually simulated and variable distances, an accommodation mea-
(Continued)

suring apparatus, a viewing direction measuring apparatus, and a control and evaluation module, which records and/or further processes the information. The accommodation of the eye can be stimulated by means of the particular test image, and the viewing direction of the eye can be measured simultaneously or in alternation, and fed to a control and evaluation module. Both eyes can be checked simultaneously by generating virtual binocular images.

19 Claims, 13 Drawing Sheets

(56) References Cited

U.S. PATENT DOCUMENTS

| | | | |
|---|---|---|---|
| 6,494,578 B1 * | 12/2002 | Plummer | A61B 3/024 351/224 |
| 7,771,052 B2 * | 8/2010 | Kratzer | 351/205 |
| 2005/0174536 A1 | 8/2005 | Hanaki et al. | |
| 2006/0244915 A1 * | 11/2006 | Clemons | A61B 3/032 351/245 |
| 2008/0246921 A1 | 10/2008 | Mihashi et al. | |

FOREIGN PATENT DOCUMENTS

| | | |
|---|---|---|
| DE | 19540802 A1 | 5/1997 |
| DE | 19704197 A1 | 8/1998 |
| EP | 2329761 A1 | 6/2011 |
| JP | H01164351 A | 6/1989 |
| WO | 2011/107244 A1 | 9/2011 |

OTHER PUBLICATIONS

International Search Report (ISR) dated Mar. 5, 2014, for PCT/EP2013/074290.

Written Opinion dated Mar. 5, 2014, for PCT/EP2013/074290.

"Shutter-Spectacle Haploscope with Eye Tracker Control for Purposes of Fusion Therapy", see Klinische Monatsblätter Augenheilkunde 2003; 220: 629-633, March.

* cited by examiner

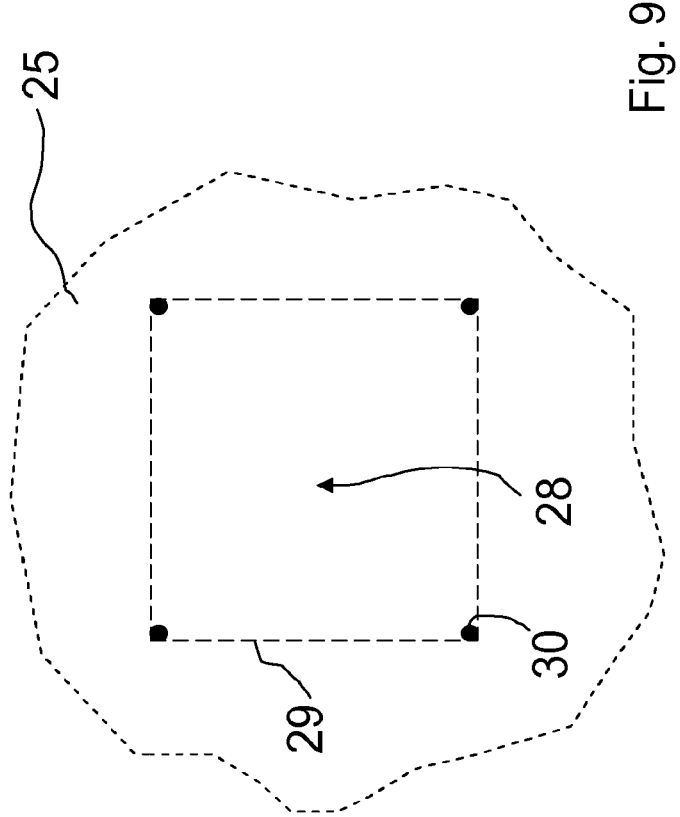

DEVICE AND METHOD FOR CHECKING HUMAN VISION

The invention concerns a device for checking human vision and a corresponding method.

BACKGROUND OF THE INVENTION

Human binocular vision is essentially determined by the motility of the eye, the fixation ability, the convergence and fusion ability, the accommodation ability and the ability of stereoscopic viewing. The basic functions are interconnected and partly interdependent through physiological and neurological processes.

The fixation ability determines how much each eye can be oriented to a fixation point, such as an object, and follow a moving object. Thanks to a neurological control loop, the eye is turned via the eye musculature so that the image of the fixation point on the retina comes to lie constantly on the fovea centralis.

The convergence ability depends on how much both eyes can be oriented to the same fixation point during binocular vision. Normally, the directions of viewing of both eyes when looking at an infinitely remote object are parallel. At shorter distance from the object, a convergence angle results between the two directions of viewing, depending on the distance of the object. Thanks to neurological control loops, the deformation of the lens is regulated by the ciliary muscle so that the fixation point is imaged sharply on the fovea centralis.

Fusion is a neurological process in which the images of the two eyes are combined in the brain into a single overall image. The result is a "3D impression". This process plays out in the brain and cannot be observed from the outside. The ability of spatial or stereoscopic vision (stereopsis) is based on the ability of the brain to ascertain depth information from the differences between the two images on the basis of the adjusted convergence angle.

The accommodation ability determines the degree to which the refractive power of the lens can be changed by means of the ciliary muscle and adapted to the particular object viewing distance, so that objects from different distance can be imaged sharply on the retina. In the relaxed state of the eye in persons with normal vision, far removed objects are sharply imaged on the retina.

Accommodative convergence means the orientation of both eyes on the same fixation point. For close objects, the eyes are turned toward the nose, so that the two lines of sight approach each other (converge) and finally intersect at the object. The angle of convergence at which the lines of sight intersect is greater as the distance is less between observer and object.

Two neurophysiological processes determine the accommodation ability of the eyes. One is based on the autofocus principle, which is also used in cameras. The focus of the eye is slightly varied and a check made to determine if the image acuity has improved or grown worse. Depending on the result, the focus is restored or the adjustment is continued until an optimum is found. This process enables a focusing of the eye during monocular vision on objects at different distance. In binocular vision, a second neurophysiological process is at work, known as near focus strias. Accommodative convergence and accommodation stand in a fixed relation to each other, described by the so-called AC/A quotient. The near focus strias always "strives" to adjust this constant optimal value. If the angle of convergence is known, the distance of the viewed object can be determined from this, and also the required accommodation from the distance. This relationship is used in the brain by the neurophysiological coupling of convergence and accommodation.

In similar fashion, the CA/C quotient characterizes the ratio of convergence accommodation (CA) to convergence (C).

Patent WO 2011/107244 A1 specifies a device for subjective refraction determination, in which several objects with different focal positions are generated and shown to the test subject for comparison. In the binocular version, however, the convergence of objects in different focal positions which is necessary for natural vision is not taken into account. The two comparison symbols are thus not represented realistically. A disturbance of the near focus strias and a falsification of the subjective refraction are therefore possible.

A device and a method for determining the subjective refraction in binocular vision are also specified in patent US 2008/0246921 A1. While this device enables a stimulation of accommodation, vision test charts are used, which cannot produce any stimulus for convergence. Neither is there any viewing direction measuring apparatus for measuring the position of the eye. Thus, a correct stimulus for the near focus strias cannot be guaranteed. Yet the correct stimulation of the near focus strias as a binocular neurological control loop can be of decisive significance for just such a subjective binocular refraction measurement.

In patent DE 195 01 415 C2 an open view apparatus is described, in which virtual test objects can be displayed in the real environment. This is a binocular apparatus, which correctly simulated accommodation and convergence. However, accommodation and convergence are firmly coupled, so that the AC/A quotient is not variable. This is a problem, because the individual AC/A value fluctuates from one person to another on account of different eye spacings and other factors. Thus, one must expect a disturbance of the B near focus strias in persons with especially large or especially small eye spacing. Neither is it possible to simulate unnatural AC/A quotients, such as occur with virtual environments such as 3D movies or 3D television. Moreover, separate focusing for both eyes cannot be done. The accommodation cannot be measured with the apparatus, and the convergence can only be determined indirectly and subjectively.

U.S. Pat. No. 5,825,456 A specifies an apparatus for generating stereoscopic images in which convergence and size of the object are varied and compared to reference objects. It is supposed to investigate how a subject perceives relative and absolute distances subjectively. The device is in the form of spectacles and it generates a variable stereoscopic test character by means of displays. At the same time, eye-trackers ("gazing point detecting") are used to determine the fixation points of both eyes. However, there is no variation of the focal position. Thus, the lack of an accommodation stimulus results in an unnatural AC/A value. Thus, an unnatural vision condition is produced, which disturbs the near focus strias. Hence, it is also likely that the subjective distance perception investigated in the patent is falsified as a result.

A publication on a clinical trial describes a "Shutter-Spectacle Haploscope with Eye Tracker Control for Purposes of Fusion Therapy", see Klinische Monatsblätter Augenheilkunde 2003; 220: 629-633. With a shutter-spectacles and a computer monitor a stereoscopic image is produced. Using eye trackers, the fixation and convergence of the eyes are measured. There is a stimulus and a measurement for the convergence. A feedback control occurs by computer. The accommodation is not taken into account. Therefore, accommodation and convergence do not correspond, and a disturbance of the near focus strias is possible, which can lead to a falsification of the results of the study.

The above-described methods all have the problem that an unnatural AC/A quotient is produced during the simulation of a virtual three-dimensional environment or a vision test character. The AC/A quotient, i.e., the coupling of eye convergence and accommodation, is either not considered at all or is only correctly adjusted for persons with a particular eye spacing. This can cause a disturbance of the near focus strias and thus a falsification of the measurement results. Furthermore, either the convergence or the accommodation is investigated with the described methods/layouts.

DE 197 04 197 A1 specifies a monocular or binocular arrangement for the subjective refraction determination and other visual functions making use of test subject glasses provided with laser scanners. The arrangement is used subjective refraction determination. In the binocular variant of the arrangement, a beam path is provided for each eye to generate an image on the retina of the test subject, so that the images can be presented at the same time or in alternation. In the binocular visual impression, two images are merged into one.

JP 11 64 351 A specifies an ophthalmoscopic apparatus in which each eye is coordinated with an optical system, which can be adapted to the eye spacing as well as the points of fixation for the examination by means of adjustable carriers.

Many orthoptic studies today are performed manually by subjective methods. Due to the subjectivity, a comparability of the results of different examination apparatus is not possible without limitations. A direct linkage with EDP equipment and use of the associated capabilities of remote examination (such as telemedicine) are not given. Only "snapshot" measurements are possible with the aforementioned apparatus, measurements continuous over time are not possible.

Subjective methods only enable a limited number of measurements at relatively large intervals of time. A high-resolution time analysis of the accommodation process, for example, as compared to the stimulus, is not possible. Transient process of the convergence or the accommodation cannot be measured with the mentioned apparatus.

The mentioned apparatus cannot perform dynamic cover and uncover tests to determine tropia and phoria.

SUMMARY OF THE INVENTION

The problem to be solved by the invention is to provide an improved device for examining human vision as well as a corresponding method.

The problem is solved by a device with the features described below and a method with the features described below.

The present invention makes it possible to generate a progressive series of quasi-simultaneous measurement data on the accommodation and viewing direction of an eye and provide this data for evaluation. First and foremost, the reaction times of the human visual apparatus to stimuli of the most diverse kind can be tested. The possibility exists of performing measurements which are continuous in time, also in particular those over large intervals of time. Transient processes of accommodation which occur and the fixation ability become measurable. The invention furthermore enables high-resolution time analysis of the course of certain variables, such as the accommodation in comparison to the stimulus. Dynamic cover and uncover tests for diagnosis of tropia and/or phoria can be performed. The invention makes possible better investigation of neurophysiological processes and control loops than was possible heretofore.

The present invention makes it possible to ascertain the eye motility, the fixation ability, the accommodation and the accommodative convergence in ways independent of each other, and investigate and in particular put out the stereopsis, the near focus strias and the AC/A quotient and/or the CA/C quotient in ways independent of each other.

An examination apparatus is provided with which the binocular observation, measurement and documentation of eye motility, fixation ability, accommodation, accommodative convergence and investigation of stereopsis and near focus strias as well as the determination of the AC/A quotient can be done in objective manner, simultaneously, independently of each other, and with the possibility of a high temporal resolution. A simultaneous investigation of both parameters together with the possibility of generating corresponding stimuli makes it possible to obtain comprehensive information about the strabological state of the test subject. Transient effects of convergence can be measured.

Advisedly, a control and evaluation module is used to produce test images on image-generating modules, adjust the optical components of imaging modules, control the acquisition of measured values by means of an accommodation measuring apparatus, control the acquisition of measured values by means of a viewing direction measuring apparatus and/or evaluate, visualize and/or save the measured values in memory.

The invention offers the following technical advantages of the device and the method as compared to the presently known ophthalmologic examination apparatus, each taken in itself but also in combination of all or some of them:

The invention in particular allows the creation of a variable virtual three-dimensional environment, with which various stimuli can be generated for the convergence and/or the accommodation of human vision. The stimuli for the convergence and the accommodation of human vision can be adjusted independently of one another, so that the stimulation can be done with different AC/A quotients and/or CA/C quotients.

For example, a natural visual impression can be simulated by the selection of an AC/A quotient adapted to the test subject. Alternatively, if need be, an AC/A quotient differing from this can be adjusted in order to specifically test a reaction to an unnatural stimulus.

The stimuli are generated in particular by means of a computer-based control unit with simultaneous or quasi-simultaneous measurement of convergence and accommodation as well as computer-supported acquisition, evaluation and display of the measured values.

Advisedly, the stimuli generated and the reactions of the eyes to the stimuli are plotted against each other in graphical representations.

To stimulate the vision, in particular, any given test figures for the fixation of the eyes, the convergence and accommodation, as well as for stereopsis and near focus strias are used automatically, flexibly, and at the shortest intervals of time under computer support.

Preferably, it is possible to calculate a characteristic value from a plurality of measured quantities and/or calculated values. This can be arranged, for example, on a suitable evaluation scale.

The vision testing apparatus enables in particular binocular measurements of the accommodation, the acquisition of the fixation points of both eyes, the determination of the convergence, the AC/A quotient and/or the CA/C quotient and/or the visualized comparison of stimuli and reactions, especially also in the acquisition and optionally the output/representation of the time variation after presenting the particular stimulus, since with the invention it is possible to detect the reactions of the vision apparatus to the different stimuli in objective manner and with high temporal resolution.

The vision testing device also enables, for example, a live control and tracking of accommodation, convergence and/or the viewing direction (fixation point) of both eyes on the monitor screen.

The vision testing device also affords the ability, for example, to plot the measurement results, contrast them with earlier measurements or contrast them with measured values of other patients, and diversified display options (charts, diagrams, characteristic values), including novel forms of display for a "diagnosis at a glance".

The vision testing device also enables in particular a high objectivity of the examination methods and good reproducibility of the examination conditions, as well as computer-supported automatic performance of diverse investigations on the basis of different computer programs.

The vision testing device can be built in compact design, for example, on the basis of ophthalmoscopic methods for measuring the viewing directions and the accommodation of both eyes by using infrared technology for illumination, imaging and measuring.

The vision testing device also enables, e.g., the creating of diagrams which visualize the relationship between parameters and measured quantities: fixation point coordinates (stimulus and measured quantity), convergence angle (stimulus and measured quantity), accommodation (stimulus and measured quantity), time, physiological parameters of the test subject, frequency of a measured quantity.

The vision testing device also enables in particular computer-controlled determination of tropia and phoria by dynamically performed "cover and uncover tests".

The vision testing device moreover enables, e.g., a remote control of the examination process and a remote telemedicine diagnosis.

For application in medical practice, the invention provides new capabilities and diverse benefits:

The vision testing device enables the rapid detection of strabological disorders (tropia, phoria, fixation problems, microstrabismus, etc.).

The technical recording of the examination results enables a comprehensive acquisition of disease patterns, analysis of the time course of diseases, visualization of the measurement results in clearly organized summaries (charts, diagrams, characteristic values) as well as the storing of the results in databases for comprehensive evaluations.

An outstanding benefit of the vision testing device is the ability to specifically investigate asthenopic complaints. Asthenopic complaints occur with deviations of the correspondence between convergence and accommodation, for example, also when viewing virtual three-dimensional images which are being increasingly presented to the eye thanks to the new digital media (3D movies, 3D television, computer games).

The vision testing device thanks to the flexible stimulation of the motor functions of the eyes and the associated neurological and neurophysiological processes enables special studies not heretofore possible with the existing devices and examination methods.

The instrument accommodation which often occurs during ophthalmologic examinations is prevented in the vision testing device by the controlled and independent stimulation of convergence and accommodation under simultaneous measurement and visualization of the reactions of the vision apparatus.

With the vision testing device, many different ophthalmologic examination methods can be performed with a single piece of apparatus.

The simple and automatable performance of strabological studies enables routine preliminary examinations in practice without actual orthoptists being present, on the model of the use of autorefractometers. The vision testing device of the invention can also be employed advantageously for routine exams in schools and kindergartens.

A use of the vision testing device is also significant at therapy centers and for therapy monitoring.

Expanded application possibilities result from the objectivity of the examination methods in the field of telemedicine.

Thanks to the good objectivity and reproducibility of the examination conditions, new prospects are opened up for medical research.

As regards an image-generating module, an imaging module, an accommodation measuring apparatus and/or a viewing direction measuring apparatus, a common beam path is provided in front of the particular eye or eyepiece.

Advisedly, a camera is provided, preferably a digital camera, by means of which the particular eye or a portion thereof, preferably the fundus of the eye or a portion thereof, is scanned in ongoing fashion and creates a progressive data series, by means of which the accommodation as well as the viewing direction of the respective eye can be ascertained by a computer or a common control and evaluation module. By the term camera is meant an image sensor for generating of image data. This also includes, e.g., devices for generating of image data making use of laser light.

Advisedly, a camera is provided for each beam path, i.e., for each eye, so that the examination of both eyes can be done at the same time.

Advisedly, image data is generated in the cameras which can go into a common evaluation, preferably as a continuous data stream.

Preferably, one camera is provided in common for the accommodation measuring apparatus (refractometer) and for the viewing direction measuring apparatus (eye tracker), which simplifies the hardware expense and the arrangements for evaluation of the graphic material.

Thanks to having an independent illumination module for the accommodation measuring apparatus and also separately for the viewing direction measuring apparatus, such as an IR illumination module, which is preferably realized by means of an IR-LED, it is possible to generate different imaging or illumination areas, especially on the fundus (back) of the particular eye, which are used on the one hand for detection of the accommodation and on the other hand for the viewing direction.

Advisedly, there is a photographic acquisition of measured values by the accommodation measuring apparatus and also by the viewing direction measuring apparatus, alternatively at very short time intervals. In this way, a very high data density can be achieved for the desired measured values almost at the same time.

Acquisition of the viewing direction is done in particular by ophthalmoscope on the basis of the fundus (back) of the respective eye. This has the advantage that the absolute viewing direction can be determined without calibration.

This produces the benefit that the movement of the macula can be directly detected and an microstrabismus present can be recognized in addition.

According to the invention, the accommodation of the respective eye and the measurement of the viewing direction of the respective eye is done simultaneously or progressively in alternation. In any case, a time series of measured data of the human vision in response to a special stimulus is created.

The beam paths for generating the stimuli by means of test figures through the image-generating module and the beam paths for measuring the reaction of the eye to the stimuli occur in particular on different wavelengths.

A dichroic mirror can be provided for combining the beam paths of different wavelengths.

A mask in the illumination beam path of the accommodation measuring apparatus serves to project a test pattern onto the fundus of the eye, by which the accommodation and refraction can be calculated directly by the computer from the image information in conjunction with the current setting of the optical component in the beam path.

A second illumination beam path serves in particular to illuminate a particular region of the eye independently from the projection of the test pattern, such as the fundus, and to ascertain the fixation direction, i.e., the viewing direction, by means of structures present in the illuminated region, such as retinal structure.

The common control and evaluation module can include a logic or be outfitted with or connected to a computer. It comprises output devices for storage, display and/or documentation of the measurement results. The stimuli are generated by the common control and evaluation module or by the computer, in combination with a suitable actuating electronics. In this process, it can also be provided, e.g., to make a manual selection of the stimuli directly by the examiner. Alternatively or additionally, fixed measurement procedures can also be programmed into the computer, so that examinations can be performed in automated fashion.

For the generating of the test image, the device can comprise a display of the image-generating module, in data connection with the common control and evaluation module or the computer, on which any give test images can be generated and projected onto the subject's retina by an optical beam path.

If is advisable according to the present invention to generate stimuli for eye movements, fixation, convergence independently of the stimuli for the accommodation, so that different AC/A stimuli and/or CA/C stimuli can be generated.

Advisedly, a 3D stimulation of the human eye can also be done with the method of the invention. For this, in particular, different fixation points can be generated, by which the 3D vision or depth vision can be tested, and this relative to the particular eye. Any given and different accommodation and/or convergence stimuli can be created in this way.

It is advantageous to ascertain the spacing between the two eyes, preferably by changing and registering the spacing of the beam paths.

Preferably, the stimulation of the eye movements, fixation, accommodation and/or convergence is done automatically by a predetermined program.

Because the test image has at least one and preferably a plurality of objects, such as geometrical figures such circles or the like, which are projected in the marginal region of the macula, i.e., the region of greatest density of visual cells, the method of the invention can also be used to advantage in patients with a macular disease (such as macular degeneration). Patients with no foveolar vision, but intact parafoveolar vision, can recognize objects positioned in the marginal region of the macula and gaze at the middle of the position of the objects. This substantially enlarges the area of application of the method of the invention.

In particular, the method of the invention also makes it possible to generate the stimuli for accommodation and convergence at the same time and/or also vary them independently of each other. When the aforementioned two stimuli are used in combination, they can be attuned to each other to simulate a natural stimulus by the method of the invention.

DETAILED DESCRIPTION OF THE INVENTION

Figure 1:
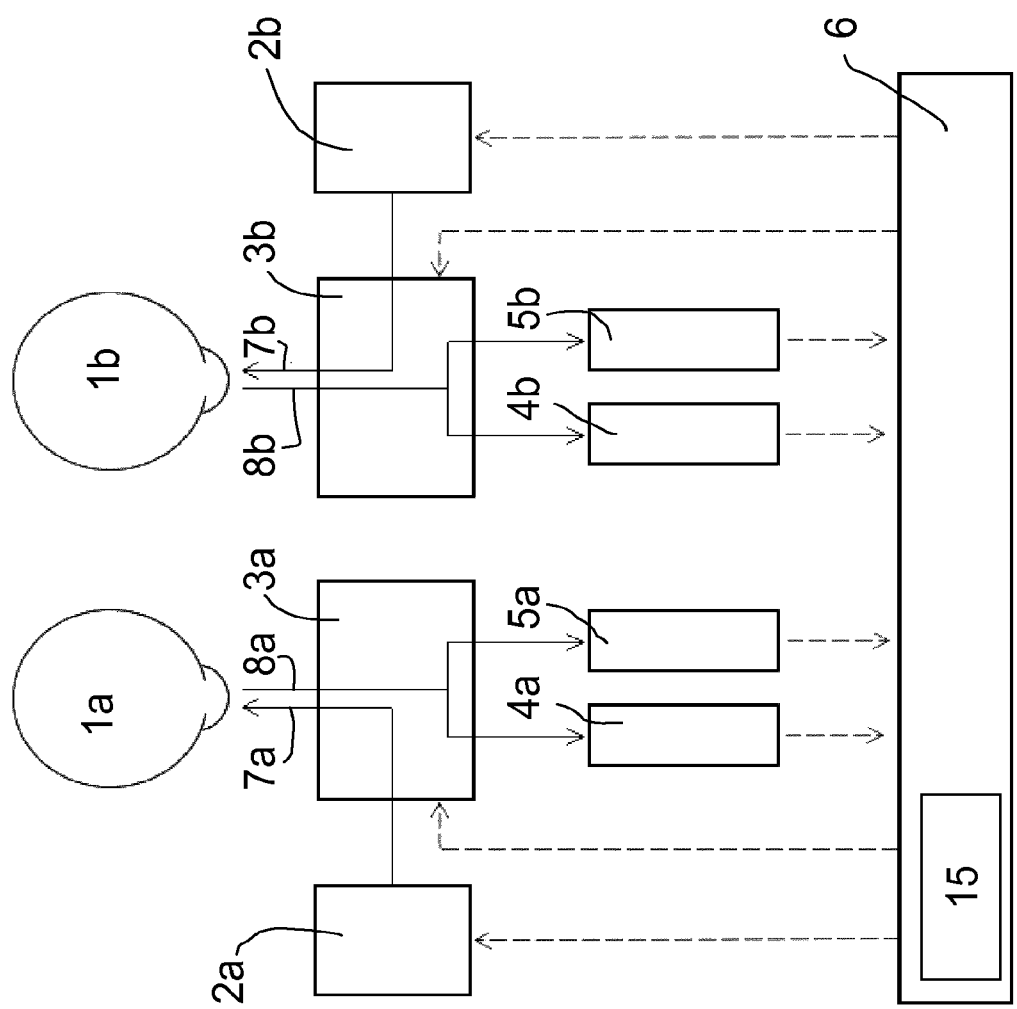
FIG. 1 a schematic diagram of the device according to the invention for analysis of convergence and accommodation of the eyes.

A sample embodiment of the invention's device for analysis of convergence and accommodation of the eyes is shown schematically in FIG. 1. It comprises image-generating modules 2a and 2b, imaging modules 3a and 3b, accommodation measuring apparatus 4a and 4b and viewing direction measuring apparatus (eye trackers) 5a and 5b, each of which is identical in construction and assigned either to the right or left eye 1a or 1b. A control and evaluation module 6 with computer 15 serves to control the components and acquire the measured values.

The components for each eye are arranged so that they are each realized by two beam paths. Stimuli for the convergence and accommodation of the eyes are generated by means of the components in the beam path 7a and 7b. The reactions of the vision apparatus to the stimuli are observed, measured and acquired by means of the components in the beam path 8a and 8b.

Figure 2:
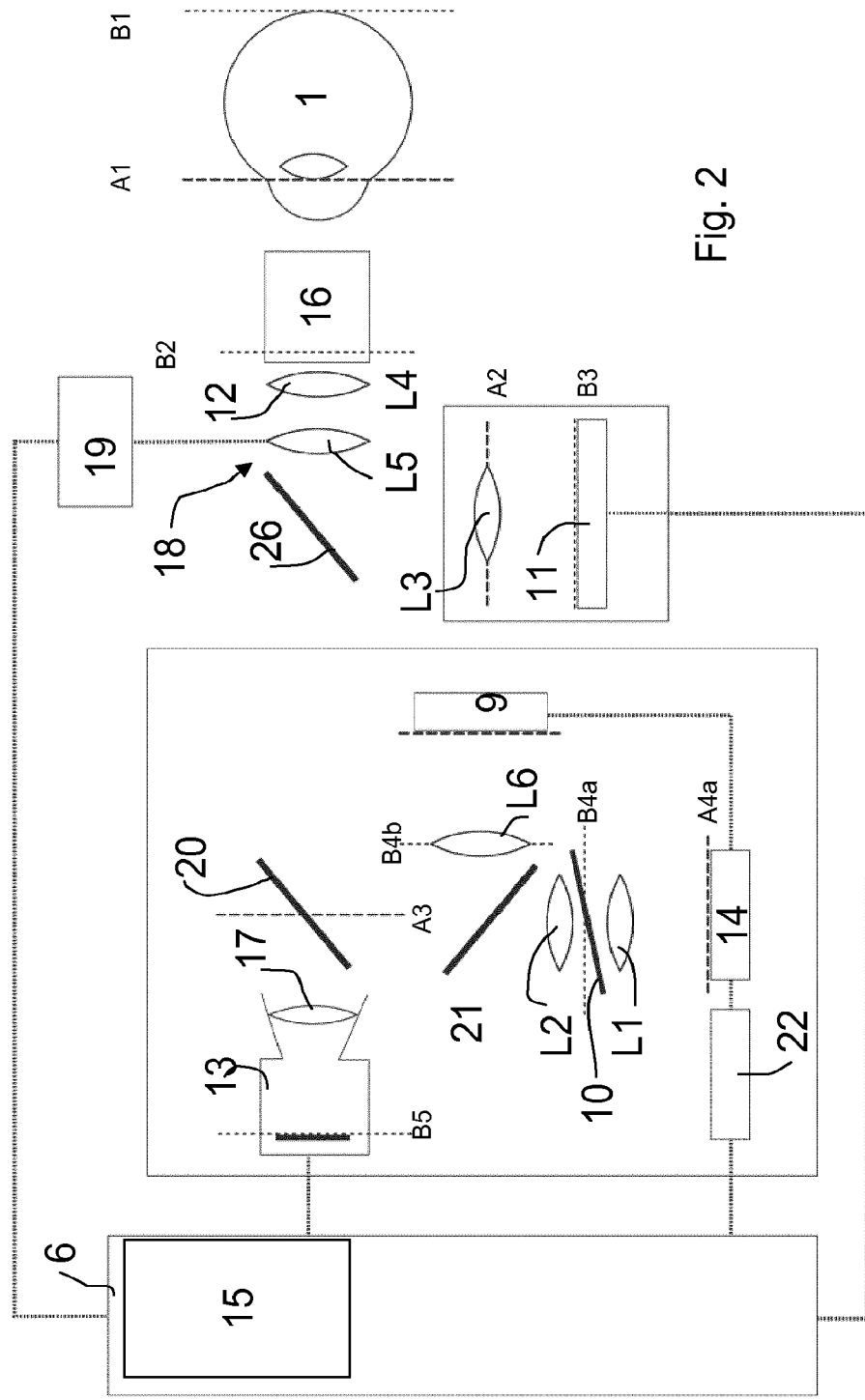
FIG. 2 the schematic diagram of one possible sample embodiment to carry out the method according to the invention.

With the help of the schematic diagram of FIG. 2, a sample embodiment of the invention's vision testing device for analysis of convergence and accommodation of the eyes and for performing the method of the invention is explained. In FIG. 2, except for a computer 15 as the main element of the control and evaluation module 6, all components for the stimulation of the vision apparatus and for acquisition of measured values are shown only for one eye. In addition to the components shown, the same components for the other eye are present and coupled in analogous manner with the control and evaluation module 6 to the computer 15.

Any given test images or test figures are generated by the computer 15 on the display 11 to stimulate the visual apparatus. The computer 15 provides various standard test figures for the examiner to use, from which he selects the test figure which is suitable for the desired examination. By displaying a light spot, one can examine the fixation ability, by displaying a fixation mark separately for both eyes the convergence, and by displaying a pair of stereo images one can examine the stereopsis.

The test figures for the right and left eye are indicated each time on separate displays 11 in immediate proximity to the eye 1, while the first eye cannot see the test figure for the second eye and vice versa.

The display 11 is situated in the image plane B3, which is projected by the lens L3 onto the image plane B2. An eyepiece 16 between eye and display 11 ensures that the display image is projected at distance. Viewed through the eyepiece 16, the test figures then appear to be at great distance on the display 11. To reduce the reflections, the lenses of the eyepiece 16 are provided with an antireflection coating (not shown in the drawing). A field lens 12 ensures that the aperture of the projection lens L3 and the aperture of the camera lens 17 are optimally projected onto the pupil of the eye 1.

For the stimulation of the accommodation, in addition to the eyepiece 16 there is placed in the beam path a focusing unit 18. As part of the focusing unit 18, a gel lens L5 is used, for example. The adjustment of the particular refractive power required for the lens is done by the actuator 19. The lens L5 can also be used to compensate for spherical vision defects. In the case of astigmatism, an additional corrective lens is required.

The focusing units 18 make it possible to vary the focus position of the test figures of the display 11 for both eyes independently of each other. Thus, the test figures indicated by the display 11 can be moved from the far point of accommodation to the near point and beyond, while at the same time varying the convergence angle.

Besides the stereoscopic distance adjustment of the eyes, which is dictated by the convergence angle and produced by the test figures separately for the two eyes (see above), a stimulus for distance perception can also be created by means of the focusing unit 18 on the basis of the focus position of the eyes. The two parameters "stereoscopic distance" and "focus distance" can be adjusted independently of each other and stimulate the corresponding reactions of convergence and accommodation.

The measurement of the fixation is done separately for both eyes by means of a viewing direction measuring apparatus 5. The viewing direction measuring apparatus 5 determines the viewing direction of an eye, e.g., by determining the corneal light reflex and/or the retinal image. By means of the measurement of the viewing directions of the two eyes, the computer 15 calculates the convergence angle. From the convergence angle, furthermore, the stereoscopic distance can be determined at which the subject has focused his eyes. In this way, one can check whether the subject is responding physiologically and neurologically correctly to the stimulus. Deviations of the relation between accommodation and convergence can be determined in time resolution and provided for an evaluation.

Insofar as is needed to test the accommodation as well as the fixation ability of only one eye, i.e., the viewing direction of the other eye is not used in the convergence determination, the device of the invention need not be binocular in design. Such a device would then have only one of the beam paths shown in FIG. 1, such as 7a and 8a, but not 7b and 8b.

Figure 3:
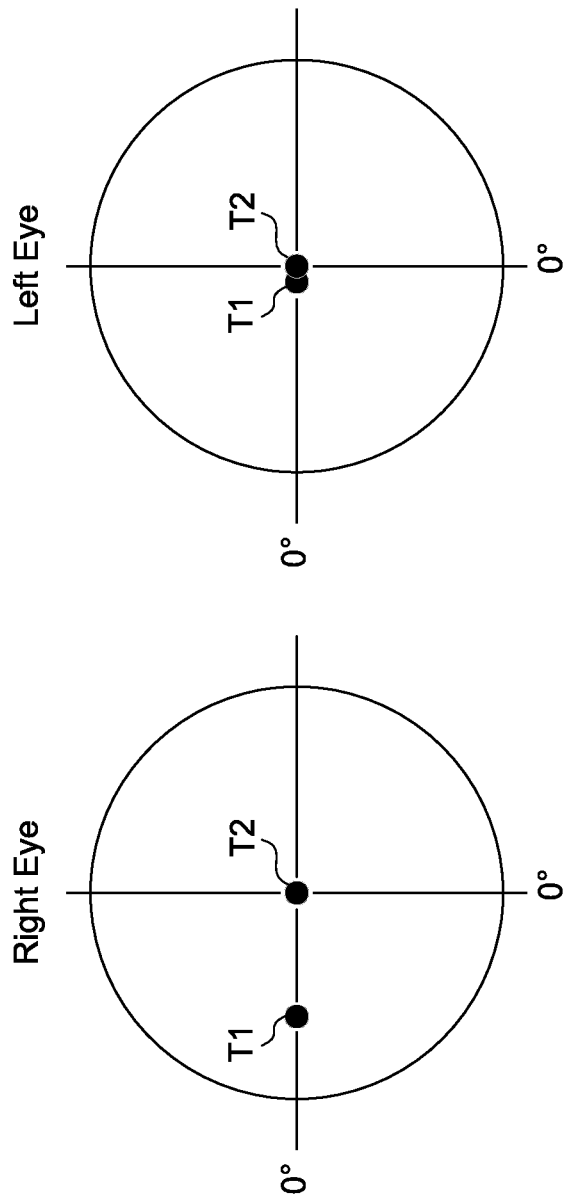
FIG. 3 an example of the detection and visualization of "transient processes" occurring during the uncover test (tuning on a stimulus for the convergence of the eyes)

Transient processes of the convergence angle and the accommodation can be recorded, resolved over time, and if necessary also sent to an output device, such as a monitor screen. As an example, FIG. 3 shows the time variation of the stimuli $D_S$ and $1/d_S$ for accommodation and convergence. Furthermore, the time variation of the measured accommodation $D_R$ and $1/d_R$, i.e., the reaction to the stimuli, are plotted. One recognizes a temporal delay $\Delta t_A$ and $\Delta t_K$ between stimulus and response. For easier reading, the vertical axis shows the reciprocal in units of meters. This value corresponds to the simulated distance at which the test figure is projected or the distance at which the subject focuses his eyes. It is likewise possible to show, in a "live" representation not presented in the figures, the time variation of the change in viewing angle on a computer display.

For the functioning of the overall procedure, the method by which the viewing direction measuring apparatus 5 operates does not need to be special. Advantageous, however, is an implementation of the viewing direction measuring apparatus 5 by an ophthalmoscope type measurement instrument for both eyes, which records the fundus of the eyes with infrared light (IR), for example. The content of the fundus image will shift analogously to a change in the viewing direction (=rotation of the eye). Thus, one can infer the viewing direction of the subject from the position of certain retinal structures (especially the fovea). A further advantage of this method is the possibility of an absolute determination of the viewing direction. Viewing direction measuring apparatus which evaluates, e.g., reflections on the cornea, is good at determining relative movements, but inaccurate in terms of absolute viewing direction. In such a case, a calibration would be necessary. With the ophthalmoscope method, on the other hand, the macula can be tracked directly, so that any microstrabismus present can also be identified.

The measuring apparatus of an eye 1 includes a digital camera 13 with objective lens 17, the eyepiece 16 in combination with the field lens L4, the mirror 20 and an infrared lighting for the fundus of the eye. The lighting comprises two beam paths, which are combined via the beam splitter 21 and deflected to the mirror 20.

One of these beam paths is produced by an illumination module 14, e.g., an IR-LED. The convex lenses L1 and L2 project the IR-LED onto the aperture plane A3. The lens L2 in combination with the lens L5 and the lens L4 furthermore projects the image plane B4a onto the image plane B2. A mask 10, which serves to create a test pattern 23 (see FIGS. 8a and 8b) on the fundus (retina 25), intersects the image plane B4a. The intersection angle between B4a and 10 is adjusted so that both planes are only slightly deviating from the parallel. Thanks to the slight slanting of the mask 10 with respect to the image plane A4a, the mask is projected onto the fundus with locally variable focus position. This is registered by the computer 15 of the control and evaluation module 6 via the camera 13 and it can calculate the accommodation and refraction from the image information in combination with the current adjustment of the lens L5.

The other illumination beam path is created by the illumination module 9, likewise an IR-LED, for example. Unlike the beam path for the determination of the accommodation, no mask is projected onto the fundus but instead a homogeneously luminous surface. Instead of the two lenses L1 and L2, only one lens L6 is used. With this illumination, the entire fundus is illuminated within the observation region, so that the retinal structures can be tracked for determining the fixation direction.

For quasi-simultaneous measurement of the accommodation and fixation direction, the computer 15 can actuate the LED driver 22 so that the camera 13 for each picture taken alternately switches on the illumination module 14 or the illumination module 9. In this way, accommodation and fixation can be determined alternately in rapid succession.

Alternatively, both illumination modules 14 and 9 can also be left on, in which case the mask 10 is projected in a retinal region which is not needed for the tracking of retinal structures to determine the fixation direction. In this case, accommodation and convergence are actually measured simultaneously.

The mirror 20 serves to separate the beam paths into an illumination beam path and an observation beam path.

The accommodation is determined with the same technology as can be used for refractometry. The accommodation then appears for an eye with normal vision in the form of an apparent near sightedness, since an autorefractometer presupposes a deaccommodated eye. This is a standard measurement technique, which is employed separately for each eye. The accommodation can be determined separately for each eye. Moreover, any vision defect which is present can be determined. This vision defect is taken into account by the computer 15 and compensated for by the stimulus unit. But this is only possible for spherical vision defects. In the case of astigmatism, the vision defect is compensated by corrective lenses. A corresponding automatic correction unit can also be used.

Ophthalmoscopy measurement techniques are used to measure both the fixation/convergence and the accommodation, employing the same components in part.

The combining of the beam paths to generate the stimuli by means of test figures and to measure the reaction of the eyes to the stimuli by the ophthalmoscopy measurement techniques is done by virtue of the different wavelengths in the two beam paths by a dichroic mirror 26.

The computer 15 is outfitted with or can be connected to output devices (not shown in FIG. 2) for storage, visualization and/or documentation of the measurement results. The stimuli are generated by the computer, in combination with suitable actuating electronics. A manual selection and control of the stimuli directly by the examiner is also possible here. Alternatively, fixed measurement procedures can also be programmed into the computer 15, so that examinations can be performed in automated fashion.

In a manual examination, the examiner interprets the reactions of the subject and possibly varies the stimuli in accordance with the goal of the study to obtain further findings.

In an automated examination, there may occur a variation of the stimuli automatically. In this case, the course of the stimulation can also be calculated in dependence on the reactions of the subject.

The measurement results of the automatic stimulus presentation are recorded and automatically evaluated. The results of the reaction measurements are either visualized in real time (live transmission), plotted as a graph for the examiner, or automatically recorded for a later evaluation. By means of suitable algorithms, the viewing directions and fixation points are determined from the fundus images. The accommodation is ascertained by evaluation the mask projected on the fundus.

The software for the instrument can be selected according to the particular application, so that the same hardware can be used for many different applications. Besides the general control of the system, the expected reactions for a healthy eye can also be calculated in advance by algorithms and compared against the actual reactions. The values found for the accommodative convergence and the accommodation are used in particular to ascertain the AC/A quotient and/or the CA/C quotient (convergence-accommodation). Finally, the difference between nominal and actual values and much more can be visualized. The spacing of the two eyes is measured each time in advance and adjusted in the apparatus.

Figure 4:
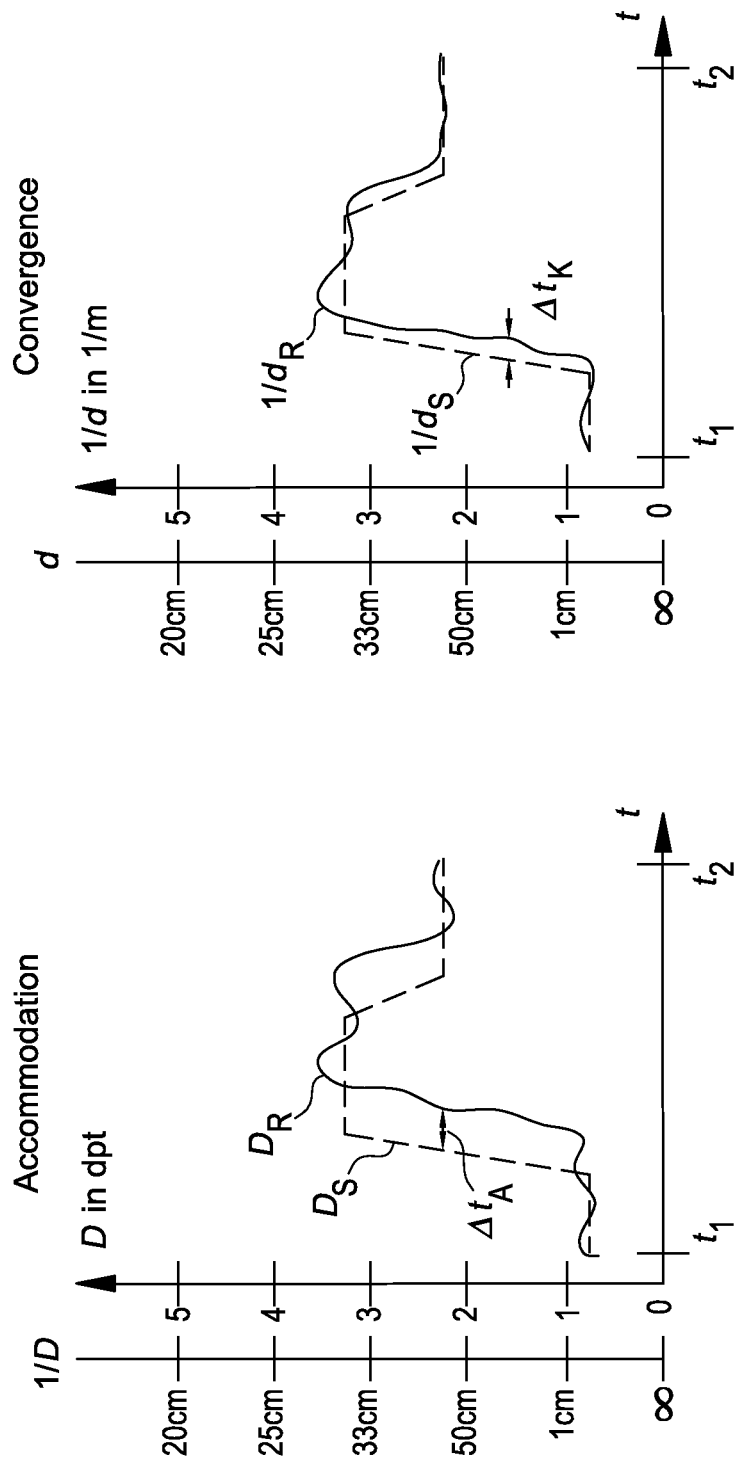
FIG. 4 a sample representation of the visualization of the focusing behavior of the eyes in response to accommodation and convergence stimuli.

An example of the comparing of nominal and actual values of accommodation and convergence taking into account the time variation (dynamics) is shown by FIG. 4. In a time region from t1 to t2, stimuli (broken line) for accommodation and convergence are generated in succession. As shown in FIG. 4, the stimuli for accommodation and convergence can correspond here in the sense of a constant AC/A value. But this need not be the case. At the same time, the reactions of the eyes are ascertained for convergence and accommodation and represented in the graph (solid line).

In the representation of FIG. 4, the accommodation value is only shown for one eye, which makes sense for subjects presumed to have similar behavior for the left and right eye. The representation of FIG. 4 shows how the human eye behaves in the case of a particular assigned stimulus relief, such as the accommodation or the convergence. The graphs shown in FIG. 4 enable a high time-resolution recording of the focusing behavior of the eyes at different distances, i.e., the plotting of the dynamic behavior of the accommodation and the convergence. Moreover, the reaction delay for accommodation $\Delta t_A$ and for convergence $\Delta t_K$ can also be determined. The transient behavior of the neurological control circuits (such as the near focus strias) can also be prominently seen in the graph in the form of the wavelike overshoots.

FIG. 5 shows the hysteresis behavior of the eyes upon presenting a stimulus for the accommodation $D_{S2}$ and for the convergence $1/d_s$ and subsequent returning of the respective stimulus to the initial condition. The stimuli for accommodation or convergence are varied over a period of $\Delta t_s$. As shown in FIGS. 5a and 5c, the relationship is ideally linear. Depending on the desired AC/A value, different slopes and thus also different limits result for $D_{S1}$ and $D_{S2}$ or $1/dS_1$ and $1/d_{S2}$, where the value D is the accommodation refractive power (units dpt or diopters) and 1/D is the accommodation distance. 1/d corresponds to D and 1/D to d. In FIG. 4 the axes of the graphs are chosen so that D and 1/d are plotted in linear manner on the particular axis.

Figure 5A:
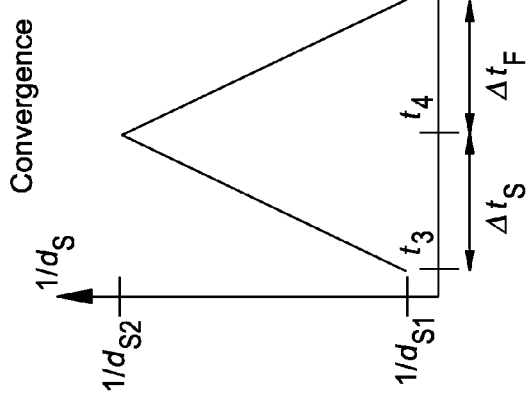
FIG. 5 the hysteresis behavior of the eyes when applying various accommodation and convergence stimuli.
Figure 5B:
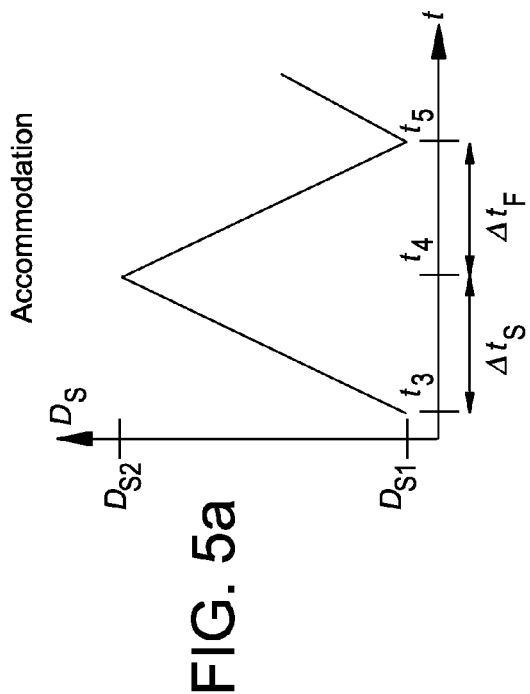
Figure 5C:
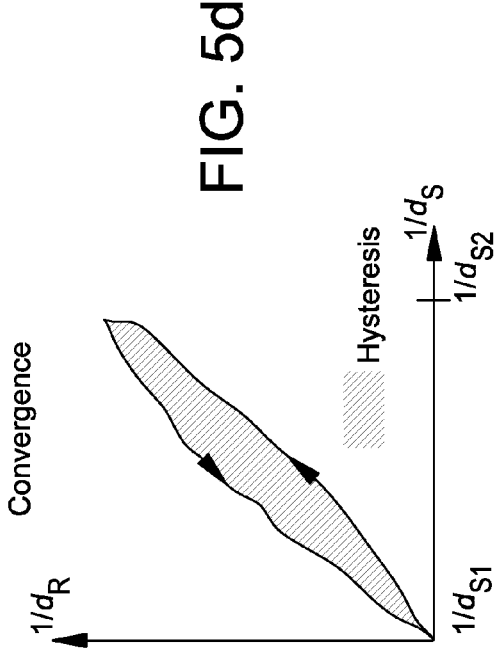

As shown in FIGS. 5a and 5c, the relationship in the variation of the accommodation and the convergence over an interval of time $Dt_s$ is linear. Depending on the desired AC/A value, different slopes and thus also different limits will result for $D_{S1}$ and $D_{S2}$ or $1/d_{S1}$ and $1/_{S2}$. If only one process needs to be examined, such as the accommodation, the value of the convergence can also be kept constant (or vice versa), so that only one of the processes needs to be examined separately.

Figure 5D:
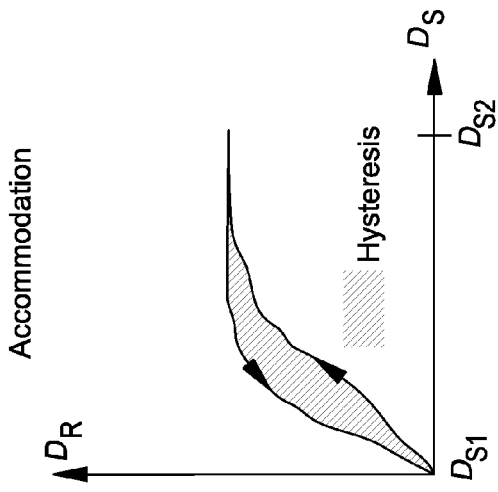

FIGS. 5b and 5d show the reactions of the human eye to the stimuli and they are preferably also displayed to the examiner. Here, the rising branch of the curve in FIGS. 5b and 5d arises in the time interval $\Delta t_s$. After this, the stimuli are again returned to the starting value in the time interval $\Delta t_F$, as shown in FIGS. 5a and 5c. This produces the decreasing lines shown in FIGS. 5b and 5d. The increasing and decreasing lines can be different and enclose an area reflecting a hysteresis behavior. The greater the area, the more pronounced the hysteresis behavior.

If desired, the measurement can also be repeated, as is indicated in FIGS. 5a and 5c.

The hysteresis behavior is to be expected on account of the reaction delays $\Delta t_A$ and $\Delta t_K$. For example, if the intervals $\Delta t_s$ and $\Delta t_F$ are smaller, the influence of the reaction delays increases and the hysteresis becomes more pronounced. Thus, with the method of the invention, in addition to the graphs of FIG. 4 one can also illustrate the time behavior of the accommodation and convergence with the hysteresis curves.

Another important piece of information in FIG. 5 is the matching of the stimuli to the corresponding reactions. For example, if one would like to reveal the static behavior of the accommodation or the convergence, the intervals $\Delta t_s$ and $\Delta t_F$ would have to be chosen very large in comparison to $\Delta t_A$ and $\Delta t_K$. In this case, the rising curve and the falling curve would be superimposed and the hysteresis area would vanish. If only the static behavior needs to be studied, the measurement in terms of $\Delta t_s$ is thus sufficient.

The control and evaluation module makes it possible to generate diagrams or tables, for example, which can show the relationships between the following parameters or measured quantities, preferably in pairs, as follows:

Fixation point coordinates, horizontal, stimulus, left eye and/or

Fixation point coordinates, vertical, stimulus, left eye and/or

Fixation point coordinates, horizontal, measured quantity left eye and/or

Fixation point coordinates, vertical, measured quantity, left eye and/or

Fixation point coordinates, horizontal, stimulus, right eye and/or

Fixation point coordinates, vertical, stimulus, right eye and/or

Fixation point coordinates, horizontal, measured quantity right eye and/or

Fixation point coordinates, vertical, measured quantity, right eye and/or

Accommodation, stimulus, left eye and/or

Accommodation, measured quantity, left eye and/or

Accommodation, stimulus, right eye and/or

Accommodation, measured quantity, right eye and/or

Time and/or

Physiological parameters of a subject or group of subjects (e.g., age, vision defect, etc.)

In addition to the above-given parameters or measured quantities or alternatively to them, quantities can also be shown in the diagrams which result from a mathematical calculation from the measured quantities, such as in particular Convergence angle, stimulus and/or Convergence angle, measured quantity and/or Vertical strabismus and/or Horizontal strabismus and/or Frequency of a quantity (for plotting the histogram).

For example, the aforementioned quantities can be represented by projection methods in the same diagram (e.g., especially in the form of a so-called 3D diagram). For example, one or more quantities and/or measured values can be visualized by an intensity value or color value in order to obtain an intensity diagram or color value diagram or a combination of the two.

FIG. 6 shows as an example how a natural stimulus can be presented by means of a test image (lead pencil) for the accommodation of the left eye, the accommodation of the right eye, and the convergence in a test subject. The index S stands for the stimulus, the index R for the reaction of the subject. The cross represents the index for the fixation point, i.e., the point of the subject's viewing direction for the stimulus presented, as measured by the viewing direction measuring apparatus.

Figure 6A:
FIG. 6 examples of investigations with natural stimulus.

FIG. 6a shows the result after presenting the stimulus to a healthy test subject. In a healthy subject, the reactions of the eyes coincide with the stimuli presented.

Figure 6B:

In the representation of FIG. 6b, an exotropia of the right eye is found in a subject. The measured viewing direction of the right eye does not coincide with the tip of the test figure (tip of the pencil).

Figure 6C:
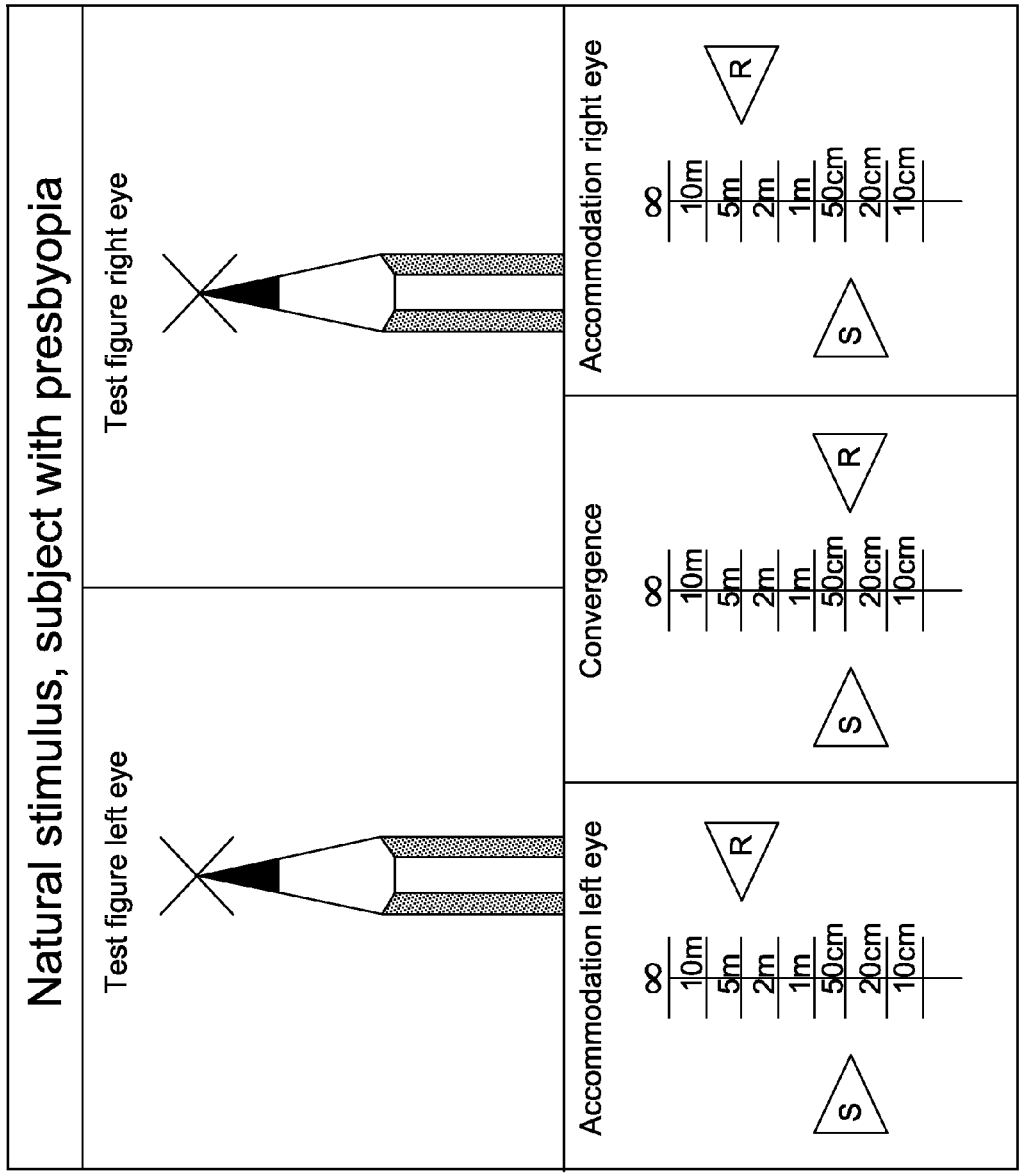

In the examination of the subject of FIG. 6c, an age-related vision defect is found (far-sighted subject), and this vision defect is present in both the right and the left eye. However, the convergence, i.e., the eye focus, is in order for this subject.

Figure 7A:
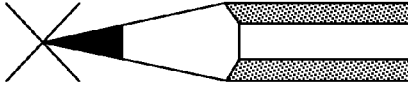
FIG. 7 examples of investigations with 3D movie stimulus.
Figure 7B:
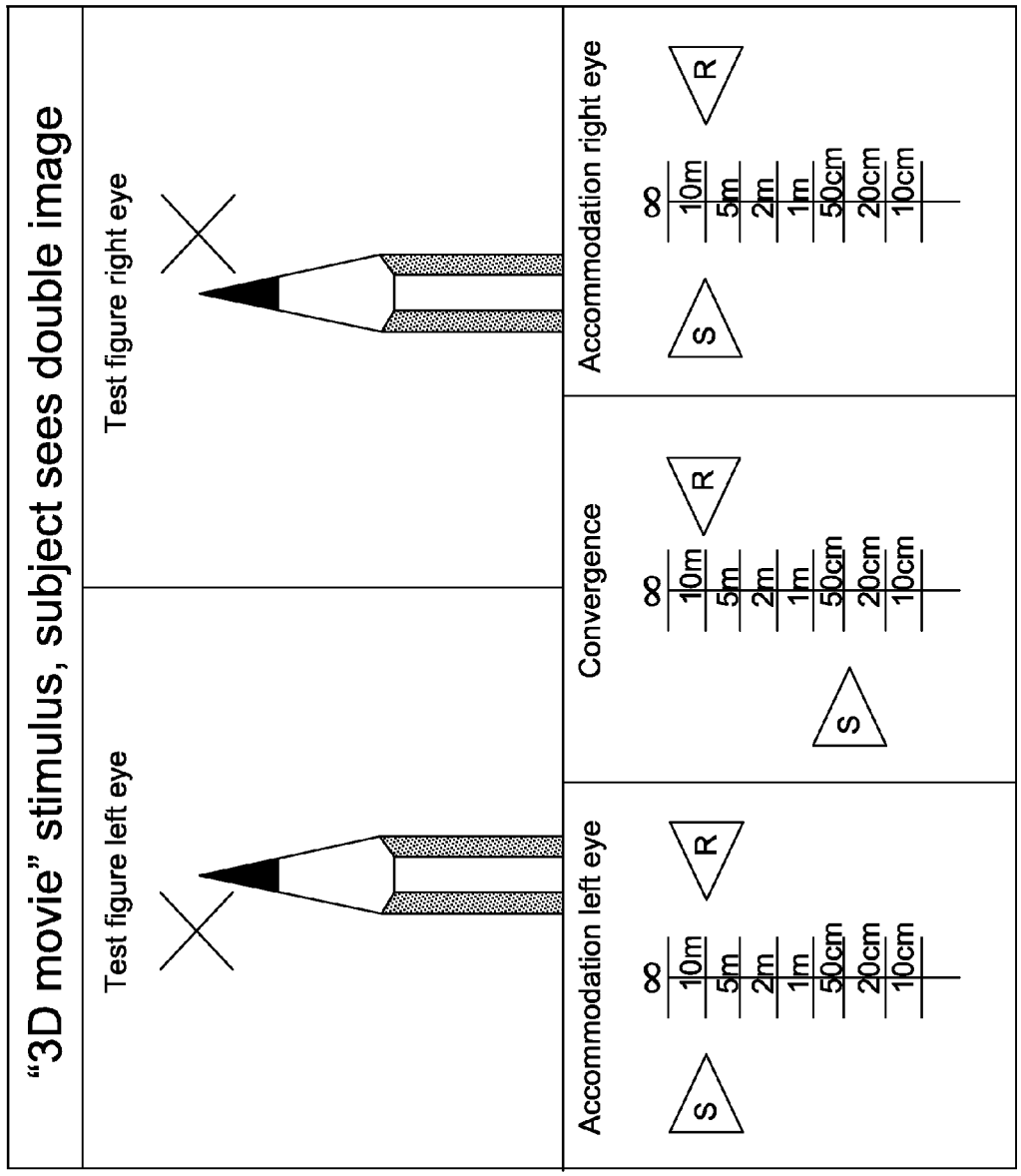
Figure 7C:
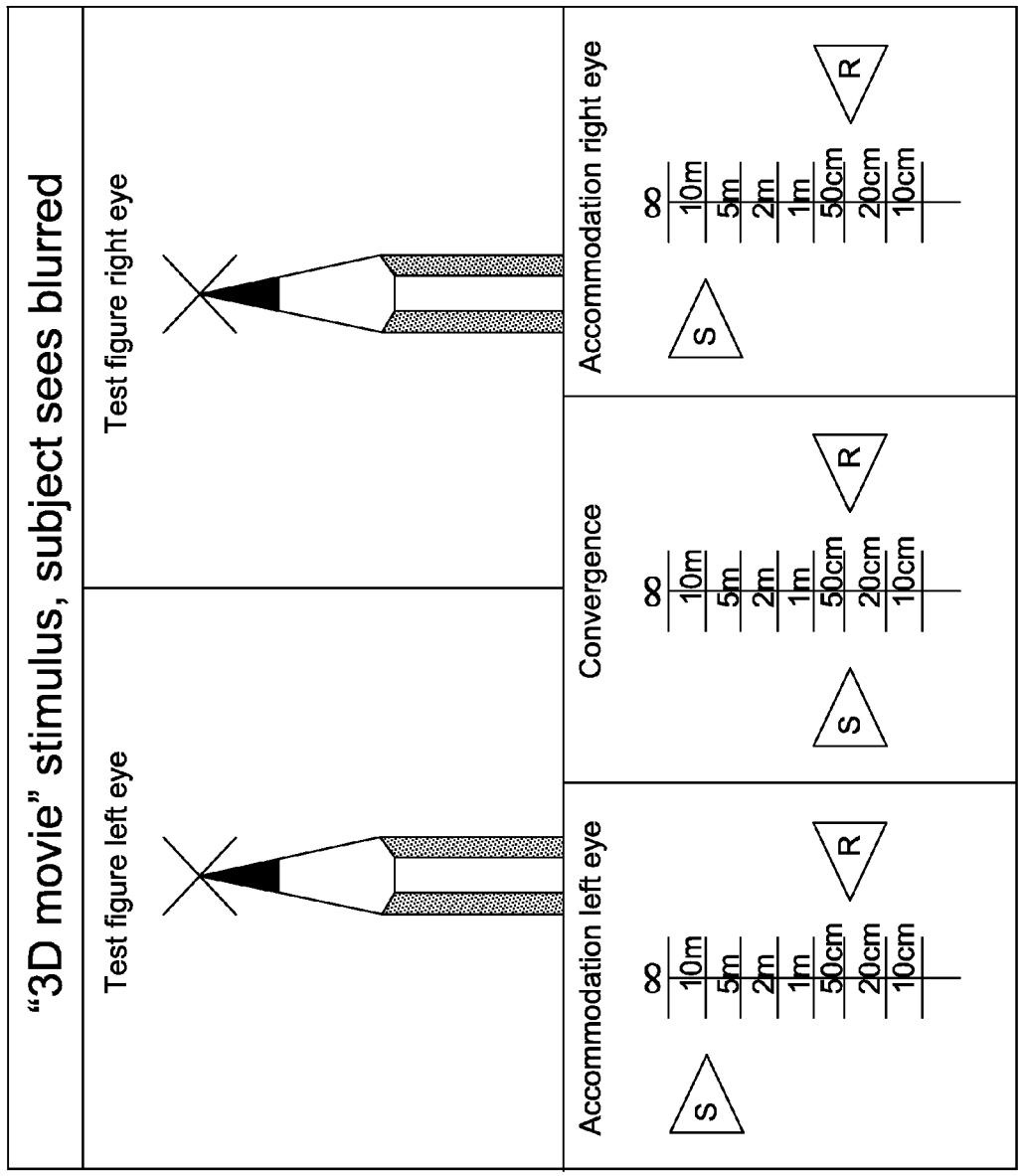

FIGS. 7a-7c show a stimulus with which the 3D vision of a subject can be tested, i.e., whether a subject is able to correctly process a virtual three-dimensional image or object as is generated in "3D movies" or "3D television". This is possible with the method of the invention by variation of the AC/A quotients. In the representation of FIG. 7a, the convergence is changed in comparison to the accommodation, by adjusting the stimulus of the convergence at a shorter distance than the stimulus of the accommodation of the particular eye. The reaction of the subject in relation to accommodation and convergence corresponds to the particular stimulus given. The subject has no problems in regard to 3D vision.

In the representation of FIG. 7b, on the other hand, a deviation is found in the reaction of the stimulus of convergence, i.e., the measured viewing directions in both eyes deviate from the actual position (tip of the pencil). The subject sees a double image.

In the representation of FIG. 7c, once again, an unsuitable accommodation is found in both eyes. The subject only sees the test image blurred, but the eye focus, i.e., fixation direction (convergence) concurs with the stimulus.

In the case of the disorders illustrated in FIG. 7b or 7c (asthenopic complaints), the method of the invention can be used to determine, during 3D viewing of a 3D film or 3D image, the viewing distance or viewing distance range at which the accommodation and the convergence are at least mostly in harmony and thus no asthenopic complaints will arise. Thus, the method can find very broad practical use.

Figure 8B:
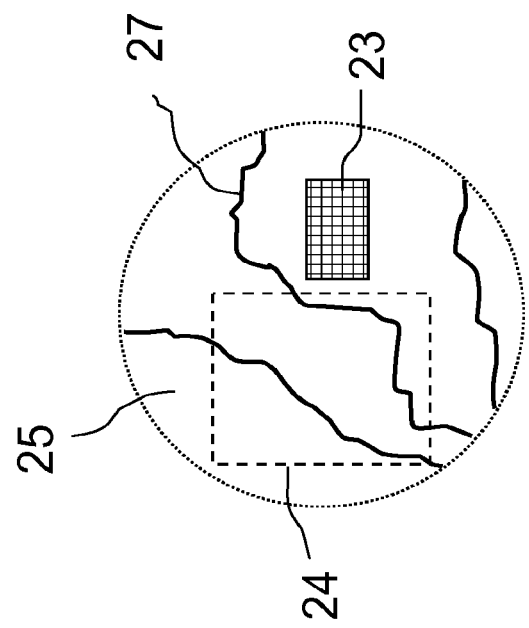
FIG. 8 a representation of various ways of arranging photographically acquired imaging regions on the retina, and FIG. 9 a greatly simplified, schematic representation of the generating of a test image with four objects, for example, which are positioned in the outer region of the macula.
Figure 8A:
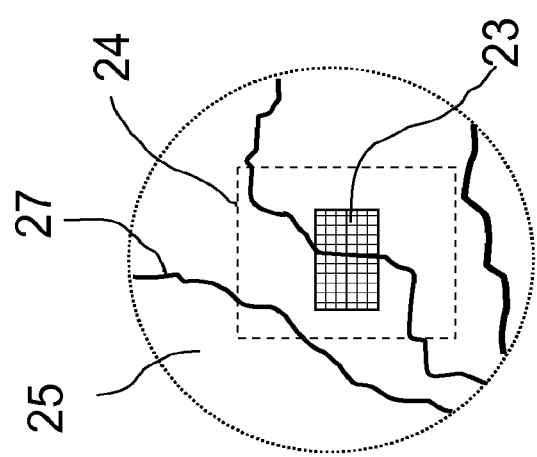

The representations of FIGS. 8a and 8b show options for the arrangement of a surface segment 24 for measuring the viewing direction (fixation) and that of a test pattern 23 projected onto the retina for measuring the accommodation within a region of the retina 25 of the human eye.

The surface segment 24 contains certain characteristics of the retina 25, such as individual blood vessels 27 running through the surface segment. By photographic acquisition of the shifting of these characteristics within the surface segment 24 caused by the viewing direction, the viewing direction can be photographically determined. Thus, the surface segment 24 is used for acquisition by means of a digital camera and evaluation by image analysis over a period of time.

The pattern 23 projected onto the retina 25 lies within the surface segment 24 in the embodiment of FIG. 8a, so that a single digital camera can be used for the evaluation of one eye by appropriate switching of the illumination modules 9 and 14 (see FIG. 2).

In the embodiment of FIG. 8b, the test pattern 23 and the surface segment 24 lie alongside each other. Here, the evaluation of the accommodation and viewing direction can be done at the same time by using two digital cameras.

FIG. 9 shows a partial surface of the retina 25, in which the macula 28 is located, i.e., the region of the retina 25 where the number of visual cells is most dense. The arrow in FIG. 9 characterizes the center of the macula 28. According to the present invention, a test image 29 can advisedly be generated in which several objects 30, such as four points as the corners of a square, are positioned in the margin region of the macula 28. A patient who during a previous test may not have seen an object located at the center of the macula 28 distinctly, can be tested with the test image 29 in regard to his vision in the margin region of the macula 28. A patient with defective foveal vision, i.e., with a degeneration of the center of the macula 28, but intact parafoveal vision, i.e., no degeneration in the margin region of the macula 28 as of yet, can recognize the four points and focus on the center of the square.

LIST OF REFERENCE SYMBOLS

1 Eye
2 Image-generating modules
3 Imaging module
4 Accommodation measuring apparatus
5 Viewing direction measuring apparatus
6 Control and evaluation module
7 Beam path
8 Beam path
9 Illumination module
10 Mask
11 Display
12 Optical component
13 Digital camera
14 Illumination module
15 Computer
16 Eyepiece
17 Camera lens
18 Focusing unit
19 Actuator
20 Mirror
21 Beam splitter
22 LED driver
23 Test pattern
24 Surface segment on retina
25 Retina
26 Dichroic mirror
27 Blood vessel
28 Macula
29 Test image
30 Object

The invention claimed is:

1. A device for checking human vision, comprising
an image-generating module for generating any test images,
an imaging module, which is configured to project a test image provided by the image-generating module as a stimulus onto a retina of an eye, wherein the imaging module contains at least one optical component having a variable focal length, so that the test image of the image-generating module is perceptible by the eye from virtually simulated and variable distances,
an accommodation measuring apparatus for measuring the accommodation of the eye,
a viewing direction measuring apparatus for measuring the viewing direction of the eye,
a control and evaluation module, which records and/or further processes the information and/or measured values originating from the individual modules and/or controls the operation sequence,
wherein the accommodation of the eye is able to be stimulated by using the particular test image, and/or the viewing direction is able to be stimulated by using the particular test image,
wherein the accommodation of the eye and the viewing direction of the eye are able to be measured simultaneously or in alternation, and
the measured values of the accommodation of the eye and of the viewing direction of the eye is able to be fed to the common control and evaluation module, and
wherein the image-generating module comprises a display for generating the test image, which is able to be actuated by the control and evaluation module, and the test image is projectable by the display into a beam path, and
wherein the viewing direction measuring device is an ophthalmoscopic viewing direction measuring device in which a movement of the retina is directly detected.

2. The device according to claim 1 wherein
separately for each eye a test image is able to be generated by a corresponding image-generating module, a projection of the test image on the retina of the respective eye can be done by a corresponding imaging module, the accommodation of the respective eye is able to be measured by a corresponding accommodation measuring apparatus and/or the viewing direction of the respective eye is able to be measured by a corresponding viewing direction measuring apparatus,
the control and evaluation module acquires and/or further processes the information and/or measured values coming from the individual modules and/or controls the operating sequence,
a stimulation of the accommodation of the respective eye can be done by means of the respective test image, and/or
a stimulation of the convergence of the eyes can be done by means of the respective test image,
the measurement of the accommodation of the respective eye and the measurement of the viewing direction of the respective eye can be done simultaneously or alternating, and
the measured values of the accommodation of the respective eye and the viewing direction of the respective eye can be sent to the common control and evaluation module.

3. The device according to claim 2 wherein each image-generating module, each imaging module, each accommodation measuring apparatus and/or each viewing direction measuring apparatus are arranged so that they establish a first beam path for the first eye and a second beam path for the second eye.

4. The device according to claim 1 wherein a progressive series of measured values are able to be generated.

5. The device according to claim 4 wherein one camera is provided in common for the measurement of the accommodation and the viewing direction of one eye and the measured values are progressively generated alternately.

6. The device according to claim 1 wherein a camera is provided for the measurement of the accommodation and/or the viewing direction.

7. The device according to claim 1 wherein a first illumination module is provided for the accommodation measuring apparatus and a second illumination module for the viewing direction measuring apparatus.

8. The device according to claim 7 wherein a mask is provided in the illumination beam path of the accommodation measuring apparatus for projecting a test pattern on the fundus of the eye.

9. The device according to claim 1 wherein an optical component is provided in the common beam path for aperture adjustment.

10. The device according to claim 1 wherein a dichroic mirror is provided in the common beam path.

11. A method for checking human vision, comprising the following steps:
generating an isolated test image using an image generating module,
projecting the test image onto a retina of a first eye,
stimulation of an accommodation by changing a focus position of the test image within a region from the far point of the accommodation to a near point of the accommodation, and
measuring the accommodation of the eye,
measuring the viewing direction (fixation) of the eye,
wherein the measuring of the accommodation of the eye and the measuring of the viewing direction of the eye is done simultaneously or progressively in alternation, and the measured values of the accommodation and the viewing direction of the eye are sent to a control and evaluation module, and
wherein the image generating module comprises a display for the generating of the test image, which is able to be actuated by the control and evaluation module, the test image is projectable by the display into a beam path and the viewing direction measuring device is an ophthalmoscopic viewing direction measuring device in which movement of the retina is directly detected.

12. The method according to claim 11 wherein:
separate generating of an isolated first test image and isolated second test image for the first eye and the second eye, respectively,
projecting of the first test image onto the retina of the first eye and of the second test image onto the retina of the second eye,
for both eyes, separate stimulation of the accommodation by changing the focus position of the test image within a region from the far point of the accommodation to the near point of the accommodation and possibly beyond,
measuring of the accommodation of the first eye and separate measuring of the accommodation of the second eye,
measuring of the viewing direction (fixation) of the first eye and separate measuring of the viewing direction (fixation) of the second eye,
calculation of the convergence angle with the aid of the measured values of the viewing direction of the two eyes, wherein
the measuring of the accommodation of the respective eye and the measuring of the viewing direction of the respective eye is done simultaneously or progressively in alternation, and
the measured values of the accommodation of the respective eye and the viewing direction of the respective eye are sent to the control and evaluation module.

13. The method according to claim 12, wherein the AC/A quotient and/or CA/C quotient is determined from the currently measured values of the accommodative convergence and the accommodation.

14. The method according to claim 11, wherein progressive series of measured values are generated, the stimuli for eye movements, fixation, convergence are generated independently from the stimuli for accommodation, so that different AC/A stimuli and/or CA/C stimuli can be generated.

15. The method according to claim 11, wherein a stimulation of spatial vision is done.

16. The method according to claim 11, wherein the stimulation of eye movements, fixation, accommodation and/or convergence is done automatically by a predetermined program.

17. The method according to claim 11, wherein a test pattern is projected onto the retina of the respective eye for measuring the accommodation, the image of the test pattern is acquired by means of a camera, preferably a digital camera, and evaluated by image analysis, and
the current accommodation of the respective eye is determined with consideration of the setting of the optical component with variable position in regard to the focal plane of the imaging modules.

18. The method according to claim 11, wherein a surface segment on the retina of the respective eye is selected for measuring the viewing direction (fixation) and the surface segment is acquired by means of a camera and evaluated by image analysis.

19. The method according to claim 18, wherein the test pattern as well as the surface segment are projected alongside each other on the retina of the respective eye.

* * * * *